United States Patent [19]
Prino et al.

[11] Patent Number: 5,605,891
[45] Date of Patent: Feb. 25, 1997

[54] USE OF POLYSACCHARIDES IN ACUTE PERIPHERAL NEUROPATHIES

[75] Inventors: Giuseppe Prino; Ennio Lanzarotti; Benito Casu; Laura Ferro, all of Milan, Italy

[73] Assignee: Crinos Industria Farmacobiologica SpA, Villa Guardia, Italy

[21] Appl. No.: 94,626

[22] Filed: Jul. 21, 1993

[30] Foreign Application Priority Data

Jul. 31, 1992 [IT] Italy ............................ MI92A1881

[51] Int. Cl.$^6$ ...................... A61K 31/715; A61K 31/725
[52] U.S. Cl. .................................. 514/54; 514/56
[58] Field of Search .................... 514/54, 56, 58, 514/59, 866, 23, 60

[56] References Cited

U.S. PATENT DOCUMENTS

| | | | |
|---|---|---|---|
| 5,236,910 | 8/1993 | Egidio et al. | 514/56 |
| 5,356,895 | 10/1994 | Ulrich et al. | 544/370 |

FOREIGN PATENT DOCUMENTS

| | | |
|---|---|---|
| 0513513 | 11/1992 | European Pat. Off. . |
| 3405240 | 8/1985 | Germany . |
| WO-A-9119787 | 12/1991 | WIPO . |

OTHER PUBLICATIONS

Fowler, *Electromyogr. clin. Neurophysiol*, "Neuropathy in Mucopolysaccharidosis Type 3", 1974, 14, 29–34.

Battaggia, *Pain*, "Effects of Hyaluronidase in Patients with Spinal Arachnoi Ditis and Peripheral Entrapment Neuropathies", Aug. 1987.

Greenhall, *Neuropathol. Appl. Neurobiol*, "Clinical and Neuropathological Observations in a Controlled Trial of Low Molecular Weight Dextran (LMD) in acute cerebral infarction", 1975, Jan. 1, (108).

*Primary Examiner*—Jeffrey C. Mullis
*Attorney, Agent, or Firm*—Nikaido, Marmelstein, Murray & Oram LLP

[57] ABSTRACT

Polysaccharides and more in particular glycosaminoglycans, their mixtures, fractions and derivatives thereof are effective agents in the therapy of acute peripheral neuropathies of traumatic and ischemic origin and in the therapy of acute peripheral neuropathies of toxic origin.

8 Claims, No Drawings

USE OF POLYSACCHARIDES IN ACUTE PERIPHERAL NEUROPATHIES

This invention concerns the use of polysaccharides as effective agents in the therapy of acute peripheral neuropathies of traumatic and ischemic origin, as well as in the therapy of acute peripheral neuropathies of toxic origin.

Ischemia of nerves or of nervous tissues can be induced essentially in two ways, or by intrinsic events such as vasculopathies or by extrinsic causes such as trauma, compression or injury.

When ischemia affects a limb it is observed that its most distal parts are concomitantly affected by functional alterations of motor and sensor nerves. In some specific cases the onset of a mononeuropathy caused by vasculopathy can be favoured by the already weak nerve vascularization, as it happens for the peroneal nerve.

Acute peripheral neuropathy occurs more generally as the sequel of the following events:

Large artery occlusion due to embolism or acute thrombosis. Ischemia usually occurs in patients affected by cardiac diseases or advanced atherosclerosis. In such cases femoral and iliac arteries are the vessels most frequently involved.

Small artery occlusions caused by traumas in the proximal parts of the limbs.

Mechanic lesion of peripheral nerves. The lesion triggers the Wallerian degeneration of the distal nerve segments. When the lesion is due to compression, axon injury may either lead to the blockade of nerve conduction (neuropraxia) or to proximal-distal degeneration of the nerve (axonotmesis).

In the art it is already known that drug effectiveness in such pathologies can be demonstrated also with experimental models of traumatic lesion.

On the issue worth mentioning is that models based on focal ischemic events are known to give unreproducible results and hence are methodologically unreliable.

The pharmacological tests more frequently used to demonstrate drug activity in peripheral neuropathies of traumatic or ischemic origin are the following:

Extent of nerve regrowth at the lesion site (in vitro test for neuritogenesis, see A. Gorio et Alii, "Experimental models for the evaluation of drugs active on neuronal plasticity" in Biological Psychiatry, Elsevier Science Publishers, vol II pages 192–194 1991). This test evidences if a drug can influence axon sprouting through the lesion site. In human acute peripheral neuropathies physiological nerve regrowth is often quite weak, and as such it doesn't usually allow the achievement of nerve regeneration at a significant extent.

Neuroprotection of the nervous tissue after a lesion induced by trauma, or by administration of a neurotoxic substance (Di Giulio et Al., Brain Res. 342 405–408). The test appears very crucial for the assaying of drug activity, since the further step of nerve regeneration depends upon neuron survival.

It has already been recognized the biological importance that amongst polysaccharides, there are sulphomucopolysaccharides, or glycosaminoglycans, which are polymers contained in the extracellular matrix of all connective tissues.

Worth saying is that their specific function in the extracellular matrix hasn't been yet established, since in this field so far attention has been given mainly to proteoglycans, that are macromolecular aggregates containing glycosaminoglycans and proteins, found particularly abundant in connective tissues.

Therefore for sulphomucopolysaccharides the available information allows one to draw a very limited picture on their role in nervous cell physiology.

Quite recently it has been proposed that these polymers do influence the embryonic morphogenesis of tissues. In a paper of P.E. Brittis "Chondroitin sulfate as regulator of neuronal patterning in the retina" Science, 255 733–736 1992, evidence has been given to the role of this polymer in the regulation of cellular development and differentiation in embryonic retina. Said otherwise, from this work it is concluded that chondroitin sulfate might influence biological specialization of formerly non-differentiated embryological cells.

For what concerns the therapeutic use of glycosaminoglycans in the specific field of neuropathies, worth mentioning here is that in the state of the art, and in particular in EP-A-0513513, it is disclosed that glycosaminoglycans are active in the treatment of diabetic neuropathy.

Said activity was demonstrated with an experimental model wherein diabetes was induced in male albino rats by a subcutaneous injection of alloxan.

Animals were sacrificed after 18 weeks. From the gut were then taken the duodenum and jejunum, which were dissected into small pieces and subsequently determined by radioimmunoassay thereof was the content of Substance P and Met-Enkephalin. Results of the above determinations showed that the diabetes-induced decrease of both neuropeptides was substantially prevented by pharmacological treatment with glycosaminoglycans (subcutaneous route at doses of 6 mg/Kg/die or 15 mg/Kg/die, according to the polymer being therein considered).

This prior art with respect to a first consideration should be made on the time of diabetes inducement envisaged in the above patent application.

As a matter of fact the information available in the literature of this field makes it possible to draw a quite definite correlation between the time of diabetes inducement and alterations in nerve physiology.

For instance in the paper of Sharma A.K., Thomas P.K., "Peripheral nerve structure and function in experimental diabetes" J. Neurol. Sci. 23 1–15 1974 it was demonstrated that after a time varying approximately from 6 months to 1 year from experimental alloxan - streptozotocin induction of diabetes in rats, although there was observed a substantial reduction of motor nerve conduction velocity, not any significant lesions were instead detectable in nerve structure morphology.

Worth saying also is that axonal disease, which is a typical feature of the chronic state of the pathology, occurs in alloxan diabetic rats after 16–18 months (Powell et Alii, Acta Neuropathol. 1984 65: 128–137).

On the basis of the above information it is concluded that the period of 18 weeks being adopted in the alloxan induced diabetes experiment featured in EP-A-0513513, is evidently too short for allowing the appearance of any severe nerve lesions.

Consequently the practised artisan in these conditions wouldn't have been able to draw any conclusion whatsoever on the activity of glycosaminoglycans in acute peripheral neuropathies, as has been demonstrated in the experiments herebelow reported.

Moreover also the same evidence given in EP-A-0513513 on the increase of neuropeptide levels being provided to support glycosaminoglycan activity may be reputed as not yet convincing for assessing the therapeutic effectiveness of said compounds.

As a matter of fact, from the art it appears that the pharmacological methods usually adopted in such connection are anyway different from that referred to in the above patent application.

For instance In the paper of K. Suzuki "Gangliosides and neuropathy", pages 531–546 (page 532 in particular) of the book "Gangliosides and modulation of neuronal function", Hinrich Rhamann Editor, Springer Verlag 1987, it is reported that the pharmacological methods for screening activity in diabetic neuropathy are the following: nerve conduction velocity, brainstem and cortical auditory evoked potential, axon diameter, internodal distance, the structure of myelin, re-innervation of injured nerves.

Substantially in the same sense is the paper of A. Gorio "Pharmacological aspects of peripheral neuropathy" and in particular the paragraph "Diabetic neuropathy" at pages 32–33 of the proceedings from the "International Conference on peripheral neuropathies 24th–25th Jun. 1981 -Madrid " Excerpta Medica International Congress Series 592 1981.

Similar conclusions can be drawn also for another class of compounds used in the therapy of diabetic neuropathy, i.e. aldose reductase inhibitors.

The pharmacology of said substances, as from the rewiew of Paul Benfield "Aldose reductase inhibitors and late complications of diabetes" Drugs 32 (Suppl. 2) 43–55 (1986), evidences that the experimental model of nerve conduction velocity was indeed that primarily used to show their activity in diabetic neuropathy.

Further support to the importance of the axonal transport experimental model in connection with diabetic neuropathies is moreover given in the paper of A. Gorio et Al. "Pharmacology of nerve regeneration" in the book "Neuroregeneration" edited by A. Gorio, Raven Press, pp. 289–320 (1983).

Coming now to illustrate the object of this invention, it is herebelow demonstrated that in the in-vitro experiment of neuritogenesis polysaccharides do antagonize the inhibitory effect of PMA (4b-phorbol-12b-myristate-13a-acetate) on neurite or axon formation in neuronal cells.

Further on in the disclosure it is shown that in in-vivo experiments the same compounds do counteract the morbidity induced on the nervous system of rats by a traumatic injury or by administration of a nerve toxic compound.

The substances examined in the aforementioned experimental tests are reported in the following tables I and II.

It must be pointed out that in the particular case of sulphomucopoly- saccharides the analytical features of the preparations being given in said tables should be looked at as pure objective evidence that the polymer being used in the experiment falls within the definition given in the art for the glycosaminoglycan in question.

As a matter of fact, to the practised artisan it is very well known from quite a number of papers what is meant by the term heparin or, respectively, heparan sulfate, chondroitin sulfate A or chondroitin 4 sulfate, chondroitin sulfate C or chondroitin 6 sulfate, dermatan sulfate or chondroitin sulfate B.

To give a suitable example of this are herebelow cited the following references:

For heparin: B. Casu: "Structure and biological activity of Heparin" Advances in Carbohydrate Chemistry 43 51 1985.

For hyaluronic acid, chondroitin sulfates A and C, dermatan sulfate, heparitin sulfate:

J.E. Scott: "Aliphatic ammonium salts in the assay of acidic polysaccharides " Methods of biochemical analysis vol. 8 pages 148–149 1964.

U Lindhal et Al. : "Glycosaminoglycans and their binding to biological macromolecules" Annual Rewiew of Biochemistry 47 pages 387–390 1978.

R. Varma et Al.: "Mucopolysaccharides - glycosaminoglycans of body fluid in health and disease" (De Guyter ed.) pages 8, 12–18, 20–23 1983.

For heparitin sulfate see also R. Linker et Al.: "Heparitinsulfate " B.B.A. 29 443 1958; J.S. Brimacombe: "Mucopolysaccharides (Elsevier Publ. Company) pages 138–140 (1964).

The same proposition applies also to those polysaccharide derivatives, such as pentosan polysulfate, which are known since long ago in this technical field and the most important chemical and physico-chemical characteristics of which are already of record in the more diffused and authoritative books of the relevant art.

As an example of this can be herein cited the Index Merck, 10th Edition.

For the other compounds of tables I and II thereof references to the art or methods used for their isolation are herebelow given.

Fast moving and slow moving heparin were prepared in Crinos Laboratories from a batch of lung heparin according to the method of B. Casu et Al., Arzneim. Forsch./Drug Res. 36(I) 4 637–642, 1986.

Heparin derivative obtained by oxidizing the polymer with sodium periodate and following treatment with sodium borhydride was prepared according to the process described in the Prior Art.

The glycosaminoglycan mixture assayed in the following pharmacological experiments was prepared on a laboratory scale by extracting 50 Kg of organ at a time, duodenum or alternatively small intestine, following substantially the procedure disclosed in U.S. Pat. No. 3,936,351.

Heparin which was further sulphated was prepared according to the method described in the paper of A. Naggi et Al.: "Supersulfated heparin fragments, a new type of low-molecular weight heparin" Biochem. Pharmacol. 36 12 1985–1900 1987.

The electrophoretic method used for the quantitative analysis of the glycosaminoglycan mixture was basically that described by R. Cappelletti et Al., Anal. Biochem. 99 311–315 1979, wherein the following experimental conditions were instead adopted:

First electrophoretic run: barium acetate buffer 0,1M pH 5, applied voltage: 150 V for three minutes.

Second electrophoretic run: the buffer used was a mixtures of barium acetate buffer 0,1M and ethanol in the ratio 100:3 (vol/vol), applied voltage: 150 V for 20 minutes.

Third electrophoretic run: the buffer used was a mixture of barium acetate buffer 0,1M and ethanol in the ratio 100: 20 (vol/vol), applied voltage: 150 V for 20 minutes.

Standard samples of the glycosaminoglycans used in the electrophoretic analysis were characterized at Ronzoni Institute (Milan, Italy).

TABLE I

| COMPOUND | Mol. Wt. × 10³ | Total sulfur % by wt. | Molar ratio groups $SO_3^-/COO^-$* | Manufacturer, batch number, other chem. parameters, notes |
|---|---|---|---|---|
| Heparin | 14 | — | 2.1 | Sigma, code n. H 7005 |
| Fast moving heparin ( abbr. HPFM ) | 6 | — | 1.8 | Crinos Res.Lab. batch n. V0161C |
| Slow moving heparin ( abbr. HPSM ) | 18 | — | 2.2 | Crinos Res.Lab. batch n. V0174B |
| Low molecular weight heparin | 4.5 | — | 2.5 | Sigma, code n. H 5640 |
| Sulphated heparin | 4.8 | — | 3.5 | Ist. Ronzoni, batch n. G 1079/7 |
| NaIO4-oxidized and NaBH4-reduced heparin | 9.9 | — | 2.2 | Ist. Ronzoni, batch n. G 1160/B |
| Heparitin sulfate ( abbr. HS ) | 13 | — | 1.6 | Syntex, batch n. 911013/B |
| Low molecular weight heparitin sulfate | 7.5 | — | 1.4 | Sigma, code n. H 5393 |
| Glycosaminoglycan mixture ( abbr. GAG mixture ) batches: | | | | Crinos Res. Lab. |

| | | | | HPSM° | HPFM + HS° | Des° | CHSA + C° |
|---|---|---|---|---|---|---|---|
| GAG mixture batch n. 1 | — | — | — | 10 | 60 | 22 | 8 |
| GAG mixture batch n. 2 | — | — | — | 13 | 49 | 34 | 4 |
| GAG mixture batch n. 3 | — | — | — | 20 | 40 | 35 | 5 |
| GAG mixture batch n. 4 | — | — | — | 17 | 54 | 29 | 0 |
| GAG mixture batch n. 5 | — | — | — | 16 | 57 | 20 | 7 |

Note: the horizontal bar means that the relevant determination was not carried out.
* Moscellani G. et al., Il Farmaco Ed. Prat. 43 165–175 1988.
°Quantitative GAG electrophoretic determination. Data are given as percentage by weight. The abbreviation CHSA + C stands to indicate the overall quantity of CHSA + CHSC, that in the assay are determined together.

TABLE II

| COMPOUND | Mol. Wt. × 10³ | Total sulfur % by wt. | Molar ratio groups $SO_3^-/COO^-$* | Manufacturer, method, or other chemical parameters |
|---|---|---|---|---|
| Hyaluronic acid | 1,100 | — | — | Zanoni Lab. § batch n. 5197 |
| Hyaluronic acid N, 6 disulfate | 8 | — | 1.8 | Ist. Ronzoni batch n. G 1046 |
| Hyaluronic acid N sulfate | 18 | — | 1.1 | Ist. Ronzoni batch n. G 1045 |
| Dextran | 500 | — | — | Pharmacia batch n. NK-05613 |
| Dextran sulfate | 5 | 15.6 | — | Sigma, code n. D 7037 |
| Pentosan polusulfate | 3 | 21.9 | — | Sigma, code n. P 8275 |
| Chondroitin 4 sulfate ( chondroitin sulfate A ) | 30 | — | 1.1 | Crinos Res. Lab. batch n. V0210A |
| Chondroitin N,4 disulfate | 4 | — | 2 | Ist. Ronzoni batch n. G 1372 |
| Chondroitin 4,6 disulfate | 27.6 | — | 1.87 | Ist. Ronzoni batch n. G 1136 |
| Chondroitin 6 sulfate ( chondroitin sulfate C ) | 71 | — | 1.15 | Crinos Res. Lab. batch n. V0212A |
| Chondroitin N,6 disulfate | 7.5 | — | 2 | Ist. Ronzoni batch n. 1373 |
| Dermatan sulfate ( DeS ) | 30 | — | 1.04 | Crinos Res. Lab. batch n. V0176H |
| Low molecular weight dermatan sulfate | 6 | — | 1.1 | Ist. Ronzoni batch n. G 1395 |
| Dermatan 6 sulfate | 6.4 | — | 1.05 | Ist. Ronzoni batch n. G 1374 |
| Dermaten N,4 disulfate | 5 | — | 2 | Ist. Ronzoni batch n. G 1396 |
| Dermatan 4,6 disulfate | 25 | — | 2 | Ist. Ronzoni batch n. G 938 |

*ref Table I
§Milan, Italy

Chemical nomenclature used in the present application for sulfated derivatives of glycosaminoglycans does conform to that used in the art. On the issue reference can be for instance made to E-P-A 891086105.0.

It seems anyway worth stating here that in the disclosure of this application the name of a sulfate derivative is given by the parent polysaccharide name followed by letter N and/or number(s) 4 and/or 6. Letter N stands to indicate that substitution has taken place on the nitrogen atom covalently linked to carbon atom in position 2 of the hexosamine ring. Numbers 4 and/or 6 identify the hydroxyl groups of the same sugar being substituted with sulphate ions.

Indeed sulphation reactions leading to the glycosaminoglycan derivatives of hyaluronic acid, chondroitin sulfate and dermatan sulfate which have been herein exploited for the new proposed therapeutic use, were such as to allow introduction of sulfate groups exclusively in the pyranose ring of hexosamine, that together with uronic acid constitutes the dimeric repeating unit of such polymers.

Hyaluronic acid N,4 disulfate, chondroitin N,4 disulfate, chondroitin N,6 disulfate and dermatan N,4 disulfate were prepared according to the methods disclosed in E-P-A 891076105.0. Hyaluronic acid N sulphate was obtained according to the process described in example 6 of the same hereabove identified patent application. Chondroitin 4,6 disulfate and dermatan 4,6 disulfate were synthetized starting respectively from chondroitin 4 sulfate and dermatan sulfate, using basically the method of K. Nagasawa et Alii, Carbohyd. Res. 158 183–190 1986. In the present case reaction time and temperature were 1 hour and 0° C. respectively. The molar excess of the adduct pyridine-$SO_3$ employed herein was larger than that of the cited reference and amounted to 24 times the moles of the glycosaminoglycan dimeric saccharide unit.

In the in-vitro neuritogenesis test, neuronal cultures of neuroblastoma type SY5Y cells were used. Neurite formation was induced by omitting serum from the culture medium. As a consequence of it cell duplication stopped and cells brought about nuerite formation. After 48 hours full neuritogenesis was achieved and all SY5Y cells showed neurites.

Addition of a solution $10^{-8}$M PMA to said cultures at the point when serum was omitted from the culture medium influenced negatively neurite formation, so that after 48 hours neuritogenesis was evident only in about ,10% of said cells.

According to the above experimental model the compounds under screening were added to the culture medium together with PMA at a concentration of $10^{-6}$ and $10^{-8}$M respectively (for each concentration the experiment was repeated twice).

The data obtained were then worked up taking as 100 the average value of the neuritogenesis response given by those cultures added of PMA alone.

Thereof results are reported in tables III, IV and V.

It must be herein noted that said results cannot be explained with a supposed complexation of the polysaccharide with PMA, since tables III–V evidence that said pharmacological activity can be even inversely related to polymer concentration, which fact is obviously in total contrast with the hereabove hypothesized complexation.

It appears besides evident that said activity cannot be either attributed, as for instance it could have been erroneusly drawn from the hereabove formerly cited reference dealing with chondroitin sulfate, to the possible circumstance that said compounds can eventually influence the specialization process of formerly non-differentiated cells. As a matter of fact it appears per se quite clear that in the neuritogenesis experiment there were instead used cells which are differentiated already.

Results that have been obtained in this test evidence that polysaccharides show different activities. Heparin and glycosaminoglycan mixture batch n. 1 (table III) were the most active compounds at the lower concentration assayed ($10^{-8}$M). It must be further added that the same substances at even lower concentrations ($10^{-10}$ and $10^{-12}$M) brought about substantially the same neurite growth.

TABLE III

Resumption of neuritogenesis process in 5YSY neuroblastoma cell cultures brought about by glycosaminoglycans ( conc. $10^{-6}$ e $10^{-8}$M ) in the presence of PMA $10^{-8}$M. Compounds herein considered : heparin and derivatives thereof heparin sulfates and a glycosaminoglycan mixture of extractive origin

| Compound | Concentration | |
|---|---|---|
| ( ref. Table I ) | $10^{-6}$M | $10^{-8}$M |
| PMA | ( 100 ) | ( 100 ) |
| Heparin | 155 | 250 |
| Fast moving heparin | 130 | 117 |
| Slow moving heparin | 120 | 100 |
| Low molecular weight heparin | 105 | 168 |
| Sulfated heparin | 180 | 148 |
| Heparin oxidized with NAIO$_4$ and then reduced with NaBH$_4$ | 190 | 162 |
| Heparitin sulfate | 130 | 100 |
| Low mol. weight heparitin sulfate | 102 | 125 |
| GAG mixture batch n. 1 | 190 | 225 |

TABLE IV

Resumption of neuritogenesis process in 5YSY neuroblastoma cell cultures brought about by polysaccharides ( conc. $10^{-6}$ e $10^{-8}$M ) in the presence of PMA $10^{-8}$M. Compounds: hyaluronic acid and derivatives thereof, dextran and thereof sulfated derivative, pentosan polysulfate

| Compound | Concentration | |
|---|---|---|
| ( ref. Table II ) | $10^{-6}$M | $10^{-8}$M |
| PMA | ( 100 ) | ( 100 ) |
| Haluronic acid | 100 | 130 |
| Hyaluronic acid N,6 disulfate | 140 | 110 |
| Hyaluronic acid N sulfate | 125 | 120 |
| Dextran | 155 | 118 |
| Dextran sulfate | 160 | 130 |
| Pentosan polysulfate | 170 | 160 |

Amongst the compounds active at the dose of $10^{-6}$M GAG mixture batch n.1 and dermatan sulfate must be herein mentioned.

These findings have been further confirmed by the results obtained with experimental models wherein acute neuropathy induced in rats by a traumatic and, respectively, toxic injury.

TABLE V

Resumption of neuritogenesis process in 5YSY neuroblastoma cell cultures brought about by glycosaminoglycans ( conc. $10^{-6}$ e $10^{-8}$M ) in the presence of PMA $10^{-8}$M. Compounds: chondroitin sulfates, dermatan sulfate and derivatives thereof

| Compound | Concentration | |
|---|---|---|
| ( ref. Table II ) | $10^{-6}$M | $10^{-8}$M |
| PMA | ( 100 ) | ( 100 ) |
| Chondroitin 4 sulfate | 182 | 100 |
| Chondroitin N,4 disulfate | 140 | 107 |
| Chondroitin 6 sulfate | 114 | 129 |
| Chondroitin N,6 disulfate | 138 | 104 |
| Chondroitin 4,6 disulfate | 102 | 182 |
| Dermatan sulfate | 217 | 162 |
| Low mol. weight dermatan sulfate | 165 | 105 |
| Dermatan 6 sulfate | 114 | 142 |
| Dermatan N,4 disulfate | 116 | 104 |
| Dermatan 4,6 disulfate | 102 | 132 |

Traumatic lesion was brought about by resecting 0,5 cm of the left sciatic nerve. The proximal stump, that is the part of this nerve connected with the nervous cells, was tied at the resection site in order to prevent nerve regeneration (Di Giulio et Al., see above).

Such permanent lesion of sciatic nerve causes a retrograde alteration of sensorial axons, leading to degenerative atrophy of those which project in the median part of substantia gelatinosa of the lumbar spinal cord. Atrophy takes place after 10–15 days from axotomy and can be followed by monitoring the concomitant lowering of substance P levels, i.e. the neuropeptide contained in said axons. As a further consequence of the same lesion in the substantia gelatinosa of the dorsal horns of the lumbar spinal cord a concomitant degeneration of met-enkephalin-containing interneurons (trans - synaptic degeneration) is observed.

In conclusion said experimentally induced injury causes a severe fall of both substance P and met-enkephalin levels, being of about 50% of their corresponding average normal values.

In this experimental model were used a total of 30 rats.

Six groups of five animals each were formed after 24 hours from the traumatic event. Animals of five groups out of six were injected intraperitoneally with a volume of a saline solution comprised between 300 and 500 microliters containing, respectively, the following compounds ( one compound for each group, in brackets the corresponding administered doses in mg/Kg):

chondroitin 4 sulfate (5 mg/Kg);
heparin (0.25 mg/Kg);
glycosaminoglycan mixture batch n. 2 (0.25 mg/Kg);
glycosaminoglycan mixture batch n. 3 (1 mg/Kg);
glycosaminoglycan mixture batch n. 4 (5 mg/Kg).

Control groups were in number of two, one formed with animals that had not been treated (non-treated control group), while the other was the spared group of the six formerly injured (treated control group).

Controls were injected with saline solution. Injections were repeated once a day starting from the day following the experimental injury and were

TABLE VI

Experimental lesion of sciatic nerve. Quantity of substance P and met-enkephalin ( dosed by radioimmunoassay technique ) contained in the lumbar part of spinal cord 3 weeks after sciatic nerve resection and subsequent i. p. daily treatment with sulphomucopolysaccharides at the herebelow indicated doses.

| compound (ref. Table I) | dose/day i.p. mg/Kg | substance P ng/mg protein | met-enkephalin ng/mg protein |
|---|---|---|---|
| Untreated control group | — | 10.21 ± 0.13 | 0.44 ± 0.01 |
| Treated control group | — | 6.69 ± 0.23 | 0.33 ± 0.01 |
| Chondroitin 4 sulf. | 5 | 12.68 ± 0.80 | 0.98 ± 0.05 |
| Heparin | 0.25 | 18.49 ± 0.33 | 1.17 ± 0.09 |
| GAG mixture b. n. 2 | 0.25 | 16.99 ± 0.94 | 1.06 ± 0.03 |
| GAG mixture b. n. 3 | 1 | 12.69 ± 1.03 | 1.20 ± 0.10 |
| GAG mixture b. n. 4 | 5 | 17.14 ± 0.29 | 1.21 ± 0.04 |

( b. = batch )

suspended the day before sacrifice, which was performed three weeks after the nerve lesion.

Immediately after sacrifice the lumbar segment of spinal medulla was quickly dissected and frozen in liquid nitrogen at $-80°$ C. The neuropeptide content was determined according to the radioimmunoassay tecnique described in the paper hereabove mentioned of Di Giulio et Al. (1985). Found quantities of substance P and met-enkephalin are reported in table VI.

The results obtained afford the conclusion that glycosaminoglycans and thereof mixtures did effectively protect animals from degeneration of sensorial axons, as shown by the monitored remarkable increase of both neuropeptides levels in comparison to those of both control groups.

As a matter of fact, from the above table it is drawn that the overall quantity of said peptides is on the average from 2 to 2.5 times higher than that of the treated control group.

It besides appears that said ratios are of the same order of magnitude of those corresponding obtained for the same substances in the preceding in-vitro neuritogenesis experiment (ref. tables III–V).

Table VI shows also that heparin and glycosaminoglycan mixtures n. 2, 3 and 4 were more active than chondroitin 4 sulfate.

Concerning heparin in particular the above results can be taken as fully unexpected whether it is considered that in the state of the art have been so far given indications that some secondary neuropathies could be induced by heparin therapy at the usual administered doses (P.G. Spiegel et al., "Femoral-nerve neuropathy secondary to anticoagulation" The Journal of Bone and Joint Surgery, vol. 56-A n. 2, 425–426, Mar. 1974; M.B. Stern et Al. "Femoral neuropathy as a complication of heparin anticoagulation therapy", Clinical Orthopaedics and Related Research, n. 106, 140–142, Jan.-Feb. 1975; S. Jackson "Femoral neuropathy secondary to heparin induced intrapelvic hematoma" vol. 10/n.7, 1049–1051 1987). The efficacy of polysaccharides in restoring sensorial function, as hereabove anticipated, has been studied also with the experimental model of toxic neuropathy (Johnsson et Al., J. Neurosci. 12 459–475 1984).

Moreover the activity evidenced by polysaccharides in said experimental model constitutes, as formerly said, the second embodiment of the invention, i.e. the use of polysaccharides in the therapy of acute peripheral neuropathies of toxic origin.

It must be herein pointed out that the latter expression indicates those acute peripheral neuropathies caused by agents toxic to the nervous system, such as emetine, hexobarbital, barbital, chlorobutanol and other substances usually reported as having such a property in the manuals of diagnosis and therapy, such as for instance the Merck Manual 13th Edition, page 1471.

The model is based on noradrenaline (NA) and dopamine (DA) depletion in sympathetic nervous system of newborn rats induced by subcutaneous injection within 6 hours from birth of 6-hydroxydopamine (6-OHDA) at the administered dose of 100 mg/Kg.

12 rats were altogether treated, divided into 2 groups of 6 animals each. One group was administered the glycosaminoglycan mixture n. 5 (composition reported in table I), injected in saline solution (500 microliters) intraperitoneally at the dose of 5 mg/Kg once a day for 4 weeks. Treatment started the day after the toxic lesion. Control groups were in the number of two, i.e. a group treated with 6-OHDA (lesioned control group) and an untreated control group (control group). Immediately after sacrifice the superior cervical ganglion was dissected from each animal and then freeze-dried in liquid nitrogen and stored at $-80°$ C.

Evaluation of NA and DA was then made by HPLC assay.

Thereof results given in table VII show that polysaccharides, in particular glycosaminoglycans and more in particular mixtures of glycosaminoglycans wherein the percentage of each component falls within the herebelow given relevant limits, are effective agents also in the experimental model of lesioned nerve regeneration.

As a matter of fact, the table shows with evidence that said substances bring about a remarkable increase of both noradrenaline and dopamine in comparison with the lesioned control group.

Besides said figures are found of about the same order of magnitude of those of the untreated control group.

Concluding on the object of this invention, results from the pharmacological experiments hereabove described demonstrate that polysaccharides, and in particular glycosaminoglycans, may be used in the treatment of peripheral neuropathies of traumatic and ischemic origin and in the treatment of peripheral neuropathies of toxic origin.

TABLE VII

Toxic lesion of sympathetic system caused by 6-OHDA administration. Quantities of NA and DA assayed in superior cervical ganglion after 4 weeks from lesion and following i.p. treatment with glycosaminoglycans at the dose of 5 mg/Kg

|  | noradrenalin ng/ganglion | dopamine ng/ganglion |
|---|---|---|
| Control group | 22.5 ± 0.5 | 2.74 ± 0.11 |
| Lesioned control group | 2.11 ± 0.21 | 0.86 ± 0.08 |
| GAG mixture b. n. 5 | 12.8 ± 0.11 | 1.94 ± 0.03 |

( b. = batch )

For what concerns in particular the glycosaminoglycan mixtures featured in the preceding tables, it can be concluded that effective agents for the therapeutic uses herein disclosed can be considered those mixtures wherein the quantities of the glycosaminoglycan are comprised within the following limits: slow moving heparin: 10–20%, fast moving heparin+heparitin sulfate: 40–60%; dermatan sulfate 20–35%; chondroitin sulfate A+chondroitin sulfate C: 0–8%.

Polysaccharides may be administered by parenteral route at daily doses comprised between 1 and 1000 mg, preferably between 1 and 300 mg, taking eventually into due account the relevant provisions of the medical art.

On this issue it is important to note that heparin, as shown in the preceding tables VI, is effective even at doses lower than those administered.

The circumstance may be advantageously exploited in order to avoid those undesirable side effects due to the anticoagulating activity of this compound.

Dosage forms for parenteral use are sterile and apyrogenetic solutions of polysaccharides, stored in sealed ampoules, that can be administered by intramuscular, subcutaneous and endovenous route.

Said dosage forms may be also lyophilysates stored in sealed bottles, wherein the solid is then extemporarily dissolved by adding the sterile solvent.

The dosage forms may be formulated with excipients already known to the practised artisan.

Dosage forms for oral administration may be tablets, gelatin capsules, coated (gastroresistant) tablets or coated gelatin capsules, granulates.

The excipients to be included in such formulations are those known already in the art.

By oral route the daily administered dose is comprised between 1 and 1500 mg, preferably between 1 and 700 mg.

The polysaccharides that are advantageously employed in the therapeutic use which constitutes the object of the present invention can be moreover administered through the relevant pharmaceutically acceptable salts, very well known already in the literature of this field.

To give an example can be mentioned herein the corresponding salts with sodium, calcium or magnesium.

EXAMPLE 1

Synthesis of dermatan having only a sulfate group to the oxygen atom in position 6 of hexosamine ring (dermatan 6 sulfate).

A. Desulfation of the hydroxy group in position 4 of galactosamine (K. Nagasawa, Carbohyd. Res. 58 47–55 1977).

5 g of dermatan sulfate from pig mucosa were dissolved in 250 ml of water. To said solution were added 10 ml of Amberlite $^R$ resin in the acid form. The slurry was then stirred and filtered. The resin was thoroughly washed and the washings united to the starting solution. The pH was then brought to neutrality with pyridine and lyophilized.

The lyophilisate was dissolved in 500 ml of dimethylsulfoxide (DMSO) containing 10% (v/v) of methanol analytical grade. The pH was then brought to the value of 5 and the solution heated in an oil bath at 85° C. for 16 hours.

At the end the reaction mixture was cooled. 500 ml $H_2O$ at a temperature of +4° C. were added, and the pH corrected to 8 with NaOH. The solution was then dialyzed against distilled water by using a 3500daltons cut-off dialysis membrane and lyophilized. 3.25 g (65%) of the compound were recovered.

B. Sulfation of the hydroxy group in position 6 of galactosamine.

The reaction was carried out as described in the european patent n. 214879.

3 g of the compound isolated in the preceding step were dissolved in 150 ml of distilled water. 6 g of Amberlite $^R$ resin in the acid form were added and stirring was effected for 10 minutes. After filtering off the resin solution pH was brought to 5 with tributylamine 10% w/v solution in ethanol. The organic solvent was then removed under a reduced pressure at room temperature and the solution lyophilized. 5.05 g of desulfated dermatan tributylammonium salt were recovered, that was afterwards dissolved in 110 ml of dimethylformamide (DMF), to which were added further 50 ml of anhydrous DMF containing 4.12 g of the adduct pyridine-$SO_3$.

Reaction was allowed to occur under a slow stirring at room temperature for 1 hour, and was stopped by adding 160 ml of distilled water cooled at the tempetrature of +4° C. pH was corrected to 9 with NaOH. Under such conditions the tributylammonium salt of the final product precipitated. Decomplexation was effected by suspending the salt for three consecutive times in fresh 300 ml aliquots of sodium acetate saturated ethanol. The solid was dissolved in 0.25 M NaCl solution (200 ml ) and dialyzed against distilled water using a 3500 daltons cut-off membrane. NMR spectrum showed a signal at 96 ppm corresponding to the carbon atom in position 6 of position 6 of galactosamine substituted with a sulfate group. From the same spectrum it was drawn that the residual quantity of unreacted hydroxy groups in position 6 of galactosamine was less than 5 %.

We claim:

1. A method for treating acute peripheral neuropathies of traumatic and toxic origin in a patient in need of such treatment, said method comprising administering to said patient a therapeutically effective amount of at least one glycosaminoglycan or a pharmaceutically acceptable salt thereof selected from the group consisting of:

heparin;

heparin derivative obtained by oxidizing heparin with sodium periodate and then with sodium borohydride;

a mixture of glycosaminoglycans having a composition, in percentage by weight: 10–20% slow moving heparin, 40–60% fast moving heparin+heparitin sulfate, 20–35% dermatan sulfate, 0–8% chondroitin sulfate A+chondroitin sulfate C;

chondroitin 4 sulfate;

dermatan sulfate.

2. The method of claim 1, wherein the heparin derivative obtained by oxidizing heparin with sodium periodate and following treatment with sodium borohydride has a molar ratio of sulfate to carboxyl groups of about 2.2.

3. The method according to claim 1, wherein said at least one glycosaminoglycan is heparin or a mixture of glycosaminoglycans having the following composition, in percentage by weight: 10–20% slow moving heparin, 40–60% fast moving heparin+heparitin sulfate, 20–35% dermatan sulfate, 0–8% chondroitin sulfate A +chondroitin sulfate C.

4. The method according to claim 1, wherein said at least one glycosaminoglycan is in the form of one of its pharmaceutically acceptable salts.

5. The method according to claim 4, wherein the cation of said pharmaceutically acceptable salt is sodium, calcium or magnesium.

6. The method according to claim 4, wherein the dosage form containing the pharmaceutically acceptable salt is for parenteral or oral administration.

7. The method according to claim 6, wherein the dosage form for patenteral administration is a sterile apyrogenetic solution in sealed ampoules or a lyophilizate in sealed ampoules to be dissolved in the aqueous sterile solvent.

8. The method according to claim 6, wherein the dosage form for oral administration is a capsule or tablet.

* * * * *